(12) United States Patent
Chang et al.

(10) Patent No.: US 8,409,531 B2
(45) Date of Patent: Apr. 2, 2013

(54) METHOD AND APPARATUS FOR STORING AND DISPENSING REAGENT BEADS

(75) Inventors: Ronald Chang, Redwood City, CA (US); Douglas B. Dority, Mill Valley, CA (US); Steve Montgomery, Los Angeles, CA (US)

(73) Assignee: Cepheid, Sunnyvale, CA (US)

(*) Notice: Subject to any disclaimer, the term of this patent is extended or adjusted under 35 U.S.C. 154(b) by 0 days.

(21) Appl. No.: 12/512,926

(22) Filed: Jul. 30, 2009

(65) Prior Publication Data

US 2009/0289076 A1 Nov. 26, 2009

Related U.S. Application Data

(63) Continuation of application No. 11/146,304, filed on Jun. 6, 2005, now Pat. No. 7,575,721.

(51) Int. Cl.
| | | |
|---|---|---|
| *B01L 3/00* | (2006.01) | |
| *G01N 31/00* | (2006.01) | |
| *G01N 33/543* | (2006.01) | |
| *B65G 47/14* | (2006.01) | |
| *B23Q 7/04* | (2006.01) | |
| *B65H 3/06* | (2006.01) | |
| *B65H 3/24* | (2006.01) | |
| *B65H 3/44* | (2006.01) | |
| *B65H 1/08* | (2006.01) | |
| *B65H 3/00* | (2006.01) | |
| *G01N 1/00* | (2006.01) | |
| *G07F 9/00* | (2006.01) | |
| *G07F 11/16* | (2006.01) | |
| *B65G 59/00* | (2006.01) | |

(52) U.S. Cl. ........ 422/561; 422/500; 436/174; 436/518; 221/1; 221/8; 221/208; 221/209; 221/210; 221/217; 221/224; 221/229; 221/231; 221/264; 221/265; 221/266

(58) Field of Classification Search .................... 422/61, 422/63, 99, 100, 500; 436/174, 518; 221/208–210, 221/217, 224, 229, 231, 264–266
See application file for complete search history.

(56) References Cited

U.S. PATENT DOCUMENTS 5,447,372 A 9/1995 Araki et al.
(Continued)

FOREIGN PATENT DOCUMENTS

JP S48-111192 3/1972
(Continued)

OTHER PUBLICATIONS

International Preliminary Report on Patentability and Written Opinion of the International Searching Authority for International application No. PCT/US2006/021147, dated Dec. 21, 2008.
(Continued)

*Primary Examiner* — Dean Kwak
(74) *Attorney, Agent, or Firm* — Kilpatrick Townsend & Stockton LLP

(57) ABSTRACT

Embodiments of the invention provide an efficient and effective technique for storing and dispensing reagent beads. In some embodiments, an apparatus is provided for dispensing reagent beads contained in a bead storage device which includes a bead carrier having a plurality of wells; a plurality of reagent beads disposed in the wells; and a cover tape releasably attached to the bead carrier to cover the wells and retain the reagent beads in the wells. The apparatus comprises a channel in which to place the bead storage device with the bead carrier facing a support wall of the channel and the cover tape facing a stripping wall of the channel. The stripping wall includes a stripping gap disposed between a stripping edge and an opposite edge, and a dispense opening provided adjacent the opposite edge on a side of the stripping wall opposite from the stripping edge. The cover tape is insertable through the stripping gap to be pulled against the stripping edge to peel the cover tape from the bead carrier to move the wells of the bead carrier inside the channel toward the dispense opening and expose the wells individually to dispense the reagent beads.

20 Claims, 4 Drawing Sheets

U.S. PATENT DOCUMENTS

| | | | |
|---|---|---|---|
| 5,616,299 A | | 4/1997 | Walker et al. |
| 5,738,244 A | | 4/1998 | Charlton et al. |
| 5,885,530 A | | 3/1999 | Babson et al. |
| 6,003,577 A | * | 12/1999 | Morito .......................... 156/362 |
| 6,030,692 A | | 2/2000 | Auger |
| 6,488,892 B1 | | 12/2002 | Burton et al. |
| 6,601,729 B1 | * | 8/2003 | Papp .............................. 221/25 |
| 6,887,431 B1 | | 5/2005 | Vann et al. |
| 2003/0183553 A1 | | 10/2003 | Fujimura et al. |
| 2004/0086426 A1 | | 5/2004 | Vann et al. |
| 2004/0094152 A1 | * | 5/2004 | Harvey et al. ............ 128/203.15 |

FOREIGN PATENT DOCUMENTS

| | | |
|---|---|---|
| JP | H07-21502 B4 | 3/1995 |
| JP | H10-86597 A2 | 4/1998 |
| JP | 2001-500457 A | 1/2001 |
| JP | 2001-108687 A | 4/2001 |
| JP | 2001-235478 A | 8/2001 |
| JP | 2002-515044 A | 5/2002 |
| JP | 2002-347831 A | 12/2002 |
| JP | 2003-517581 U | 5/2003 |
| JP | 2004-512147 A | 4/2004 |
| JP | 2004-337108 A | 12/2004 |
| JP | 2004-537714 A | 12/2004 |

OTHER PUBLICATIONS

International Search Report issued in International Application No. PCT/US2006/021147, dated Sep. 13, 2007.

* cited by examiner

METHOD AND APPARATUS FOR STORING AND DISPENSING REAGENT BEADS

CROSS-REFERENCES TO RELATED APPLICATIONS

This application is a continuation of U.S. patent application Ser. No. 11/146,304 filed Jun. 6, 2005, now U.S. Pat. No. 7,575,721 issued on Aug. 18, 2009, hereby incorporated by reference in its entirety.

BACKGROUND OF THE INVENTION

This application relates generally to systems and methods for storing and dispensing reagent beads for use in analyzing a sample.

Many types of chemical reactions, such as nucleic acid amplification reactions, are important for research, medical, and industrial applications. Such reactions are used in clinical and biological research, detection and monitoring of infectious diseases, detection of mutations, detection of cancer markers, environmental monitoring, genetic identification, detection of pathogens in biodefense applications, and the like, e.g., Schweitzer et al., Current Opinion in Biotechnology, 12: 21-27 (2001); Koch, Nature Reviews Drug Discovery, 3: 749-761 (2004). In particular, polymerase chain reactions (PCRs) have found applications in all of these areas, including applications for viral and bacterial detection, viral load monitoring, detection of rare and/or difficult-to-culture pathogens, rapid detection of bio-terror threats, detection of minimal residual disease in cancer patients, food pathogen testing, blood supply screening, and the like, e.g., Mackay, Clin. Microbiol. Infect., 10: 190-212 (2004); Bernard et al., Clinical Chemistry, 48: 1178-1185 (2002). In regard to PCR, key reasons for such widespread use are its speed and ease of use (typically performed within a few hours using standardized kits and relatively simple and low cost instruments), its sensitivity (often a few tens of copies of a target sequence in a sample can be detected), and its robustness (poor quality samples or preserved samples, such as forensic samples or fixed tissue samples are readily analyzed), Strachan and Read, Human Molecular Genetics 2 (John Wiley & Sons, New York, 1999).

Reagent beads carrying a reagent are commonly used to provide the reagent for analyzing samples including, for example, analysis by nucleic acid amplification reactions such as PCR. In addition to nucleic acid amplification reactions, reagent beads may be used in a wide variety of other chemical reaction/detection methods known in the art. Reagent beads are fragile and contain static charges that present static handling problems.

BRIEF SUMMARY OF THE INVENTION

Embodiments of the present invention provide an efficient and effective technique for storing and dispensing reagent beads.

In accordance with an aspect of the present invention, a device for storing and dispensing reagent beads comprises a bead carrier including a plurality of wells; a plurality of reagent beads disposed in the plurality of wells; and a cover tape releasably attached to the bead carrier to cover the plurality of wells and retain the plurality of reagent beads in the plurality of wells of the bead carrier. The bead carrier and the cover tape each comprise an anti-static material. The cover tape is peelable from the bead carrier to expose the plurality of wells individually to dispense the plurality of reagent beads from the plurality of wells.

In some embodiments, the anti-static material comprises styrene impregnated with carbon. In specific embodiments, the cover tape is releasably attached to the bead carrier by a pressure sensitive adhesive. Alternatively, the cover tape may be heat-sealed to the bead carrier. The bead carrier preferably includes a linear array of wells spaced by a generally uniform distance. The cover tape is peelable from the bead carrier to expose the plurality of wells individually one at a time. Preferably, at least a portion of each well is transparent.

Another aspect of the present invention is directed to an apparatus for dispensing reagent beads contained in a bead storage device which includes a bead carrier having a plurality of wells; a plurality of reagent beads disposed in the plurality of wells; and a cover tape releasably attached to the bead carrier to cover the plurality of wells and retain the plurality of reagent beads in the plurality of wells of the bead carrier. The apparatus comprises a channel in which to place the bead storage device with the bead carrier facing a support wall of the channel and the cover tape facing a stripping wall of the channel. The stripping wall includes a stripping gap disposed between a stripping edge and an opposite edge, and a dispense opening provided adjacent the opposite edge on a side of the stripping wall opposite from the stripping edge. The cover tape is insertable through the stripping gap to be pulled against the stripping edge to peel the cover tape from the bead carrier to move the plurality of wells of the bead carrier inside the channel toward the dispense opening and expose the plurality of wells individually to dispense the plurality of reagent beads from the plurality of wells through the dispense opening.

In some embodiments, the stripping wall includes a spout coupled to the dispense opening and being oriented generally downward to dispense the reagent beads by gravity. A counter is coupled to a portion of the cover tape which has been peeled from the bead carrier to count the number of wells being exposed to dispense the reagent beads based on a travel amount of the cover tape with respect to the stripping edge.

Another aspect of the invention is directed to an apparatus for dispensing reagent beads contained in a bead storage device which includes a bead carrier having a plurality of wells; a plurality of reagent beads disposed in the plurality of wells; and a cover tape releasably attached to the bead carrier to cover the plurality of wells and retain the plurality of reagent beads in the plurality of wells of the bead carrier. The apparatus comprises a housing having in an interior thereof a channel in which to place the bead storage device with the bead carrier facing a support wall of the channel and the cover tape facing a stripping wall of the channel, wherein the stripping wall includes a stripping gap disposed between a stripping edge and an opposite edge, and a dispense opening provided adjacent the opposite edge on a side of the stripping wall opposite from the stripping edge; a clutch configured to pull a leading end of the cover tape inserted through the stripping gap to pull the cover tape against the stripping edge; and a wheel coupled to the clutch for turning the clutch to pull the cover tape.

In some embodiments, the clutch includes a ratchet mechanism to permit one-directional pulling of the cover tape. The wheel is exposed from the interior of the housing and sized to be rotatable by a user's finger or thumb. The stripping wall includes a spout coupled to the dispense opening and being oriented generally downward to dispense the reagent beads by gravity. The stripping edge includes a bend which bends outward from the channel and backward away from the opposite edge to guide the cover tape. The channel is generally circular in shape. The clutch is configured to pull the leading end of the cover tape inserted through the stripping gap against the stripping edge to peel the cover tape from the bead carrier to move the plurality of wells of the bead carrier inside the channel toward the dispense opening and expose the plurality of wells individually one at a time to dispense the reagent beads from the plurality of wells through the dispense opening. The wheel is configured to turn by at least about 60° to move from one well to a next well toward the dispense opening and expose the next well to dispense through the dispense opening. A counter is coupled to the clutch to count the number of wells being exposed to dispense the reagent beads based on a travel amount of the cover tape.

Another aspect of the present invention is directed to a method of dispensing reagent beads contained in a bead storage device which includes a bead carrier having a plurality of wells; a plurality of reagent beads disposed in the plurality of wells; and a cover tape releasably attached to the bead carrier to cover the plurality of wells and retain the plurality of reagent beads in the plurality of wells of the bead carrier. The method comprises placing the bead storage device in a channel with the bead carrier facing a support wall of the channel and the cover tape facing a stripping wall of the channel, wherein the stripping wall includes a stripping gap disposed between a stripping edge and an opposite edge, and a dispense opening provided adjacent the opposite edge on a side of the stripping wall opposite from the stripping edge. The method further comprises inserting the cover tape through the stripping gap; and pulling the cover tape against the stripping edge to peel the cover tape from the bead carrier to move the plurality of wells of the bead carrier inside the channel toward the dispense opening and expose the plurality of wells individually to dispense the plurality of reagent beads from the plurality of wells through the dispense opening.

DETAILED DESCRIPTION OF THE INVENTION

Figure 1:
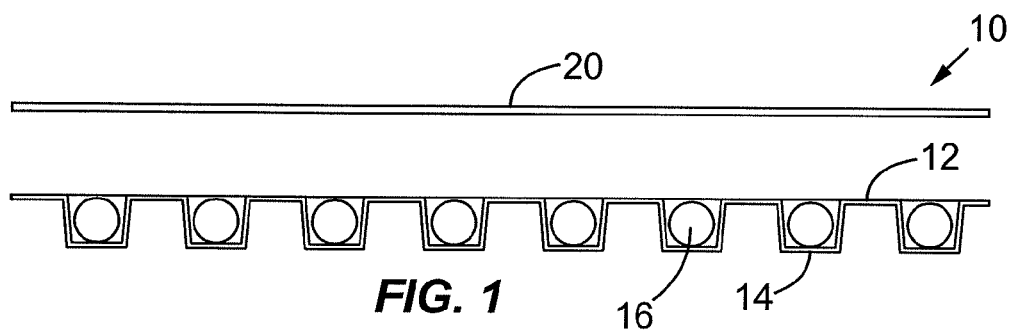
FIG. 1 is an exploded elevational view of a reagent bead storage device according to an embodiment of the present invention.

FIG. 1 is an exploded view of a reagent bead storage device for storing reagent beads to be dispensed. The storage device 10 includes a bead carrier 12 having a plurality of wells 14 and a plurality of reagent beads 16 disposed in the wells 14. The bead carrier 12 may be a flexible tape having the wells 14 formed therein, or the bead carrier may be a rigid or flexible molded part. FIG. 1 shows one bead 16 in each well 14, but the number of beads may vary in other embodiments. A cover tape 20 is releasably attached to the bead carrier 12 to cover the wells 14 and retain the reagent beads 16 in the wells 14 of the bead carrier 12. The bead carrier 12 and the cover tape 20 are made of an anti-static material. The cover tape 20 is peelable from the bead carrier 12 to expose the wells 14 individually to dispense the reagent beads 16 from the wells 14, as described in more detail below.

An example of a suitable anti-static material is styrene impregnated with carbon. Of course, other anti-static materials may be used. Examples of other anti-static materials includes, without limitation, metals and treated plastics (e.g., plastics impregnated with a conductive metal or plastics given a surface treatment). The cover tape 20 may be releasably attached to the bead carrier 12 by a pressure sensitive adhesive, or heat-sealed to the bead carrier 12. The cover tape is preferably peelable from the bead carrier using a manual force exerted by one or more fingers of the user. In FIG. 1, the bead carrier includes a linear array of wells 14 spaced by a generally uniform distance. The cover tape 20 is peelable from the bead carrier 12 to expose the plurality of wells 14 individually one at a time. Other arrangements or configurations are possible, including nonlinear arrangement of wells and nonuniform distances between wells. At least a portion of each well 14 is preferably transparent to allow one to see the content inside.

Figure 2:
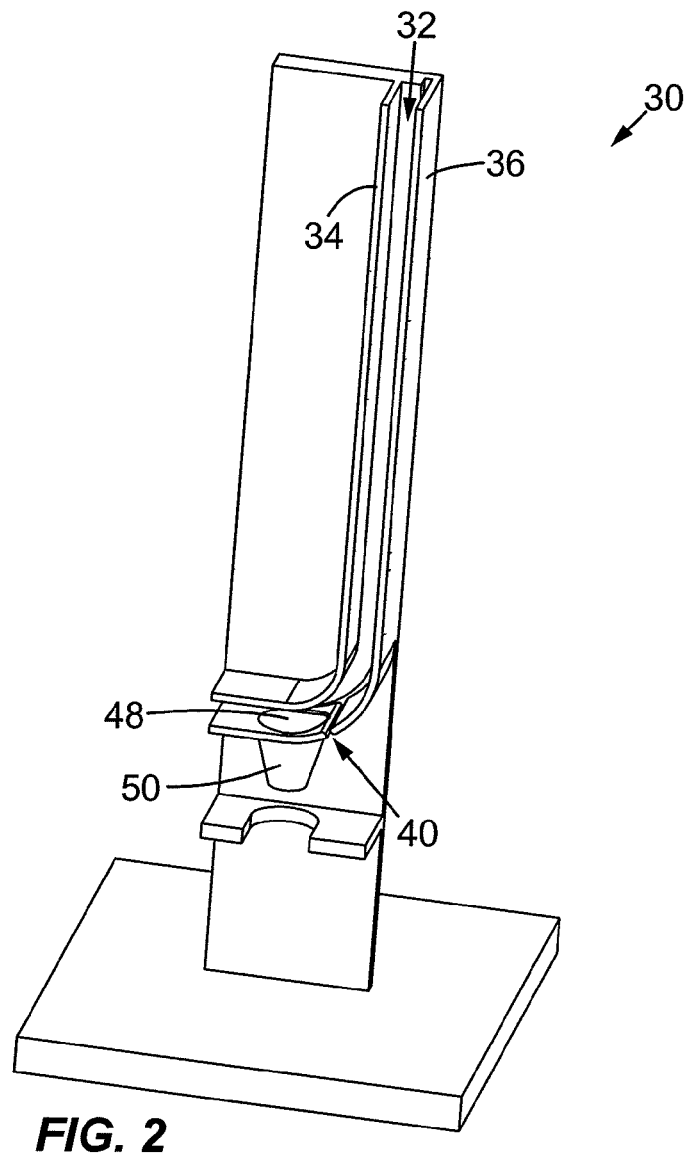
FIG. 2 is a perspective view of a bead dispensing apparatus according to an embodiment of the present invention.
Figure 3:
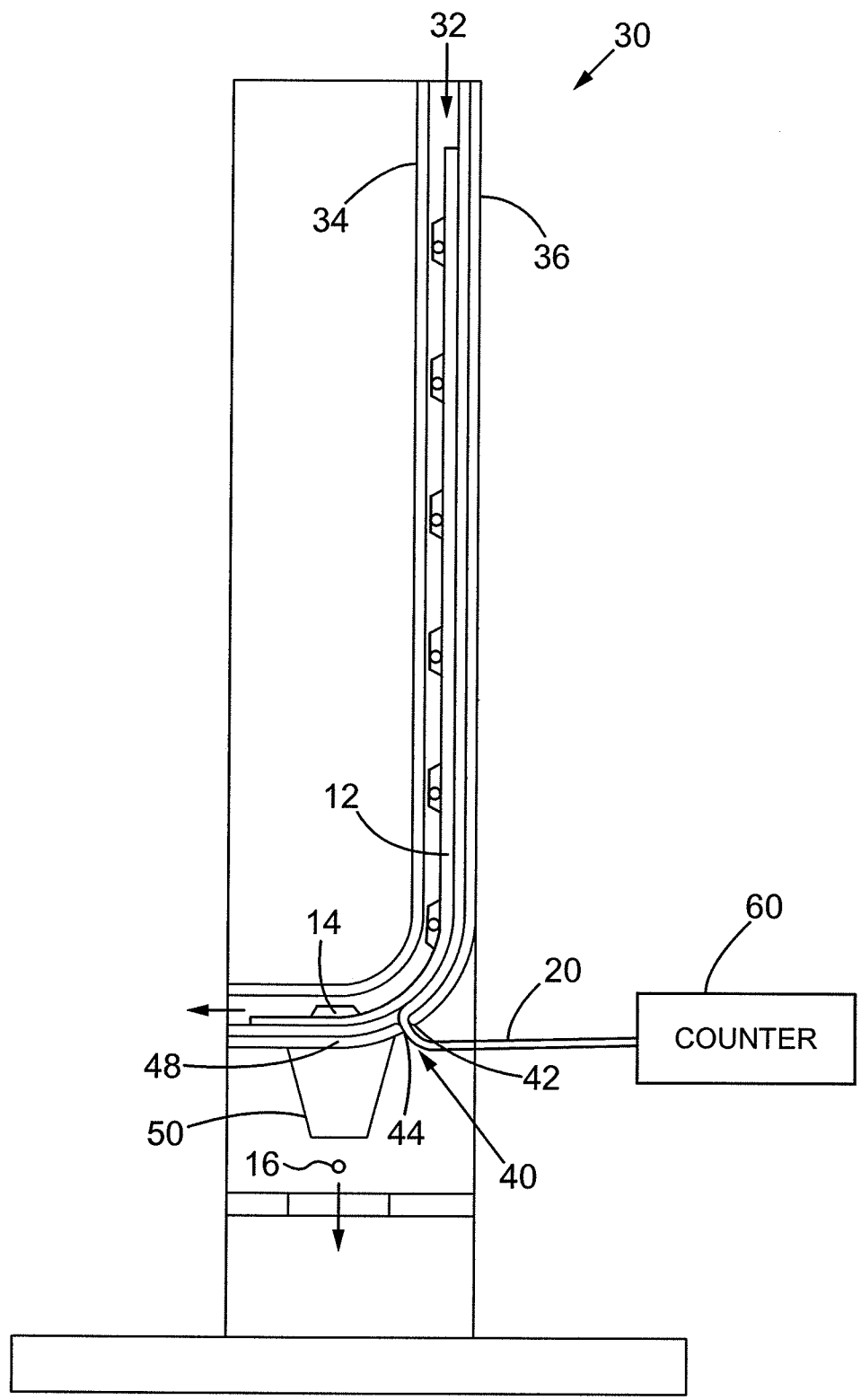
FIG. 3 is an elevational view of the bead dispensing apparatus of FIG. 2 for dispensing reagent beads from the reagent bead storage device of FIG. 1.

FIGS. 2 and 3 show a bead dispensing apparatus according to an embodiment of the present invention. The dispensing apparatus 30 can be used to dispense reagent beads 16 contained in the bead storage device 10 of FIG. 1. The dispensing apparatus 30 includes a channel 32 in which to place the bead storage device 10 with the bead carrier 12 facing a support wall 34 of the channel 32 and the cover tape 20 facing a stripping wall 36 of the channel 32. The stripping wall 36 includes a stripping gap 40 disposed between a stripping edge 42 and an opposite edge 44. A dispense opening 48 is provided adjacent the opposite edge 44 on a side of the stripping wall 36 opposite from the stripping edge 42. The cover tape 20 is insertable through the stripping gap 40 to be pulled against the stripping edge 42 to peel the cover tape 20 from the bead carrier 12, thereby moving the wells 14 of the bead carrier 12 inside the channel 32 toward the dispense opening 48 and exposing the wells 14 individually to dispense the reagent beads 16 from the wells 14 through the dispense opening 48. The stripping wall 36 desirably includes a spout 50 coupled to the dispense opening 48 which is oriented generally downward to dispense the reagent beads 16 by gravity.

As seen in FIG. 3, the cover tape 20 is pulled against the stripping edge 42 in a direction generally opposite from a direction of travel of the bead carrier 12 toward the dispense opening 48. The generally opposite direction of pulling is convenient, but not required to separate the cover tape 20 from the bead carrier 12. Other directions can work. The pulling of the cover tape 20 creates the driving force for separating the cover tape 20 from the bead carrier 12 and for moving the bead carrier 12 toward the dispense opening 48 to dispense the reagent beads 16 from the wells 14 through the dispense opening 48. A counter 60 may be coupled to a portion of the cover tape 20 which has been peeled from the bead carrier 12 to count the number of wells 14 being exposed to dispense the reagent beads 16 based on a travel amount of the cover tape 20 with respect to the stripping edge 42. This is more easily done if the distance between the wells 14 is uniform. In an alternative embodiment, a counter may be coupled to a portion of the bead carrier 12 which has been separated from the cover tape 20 to count the number of exposed wells 14.

Figure 4:
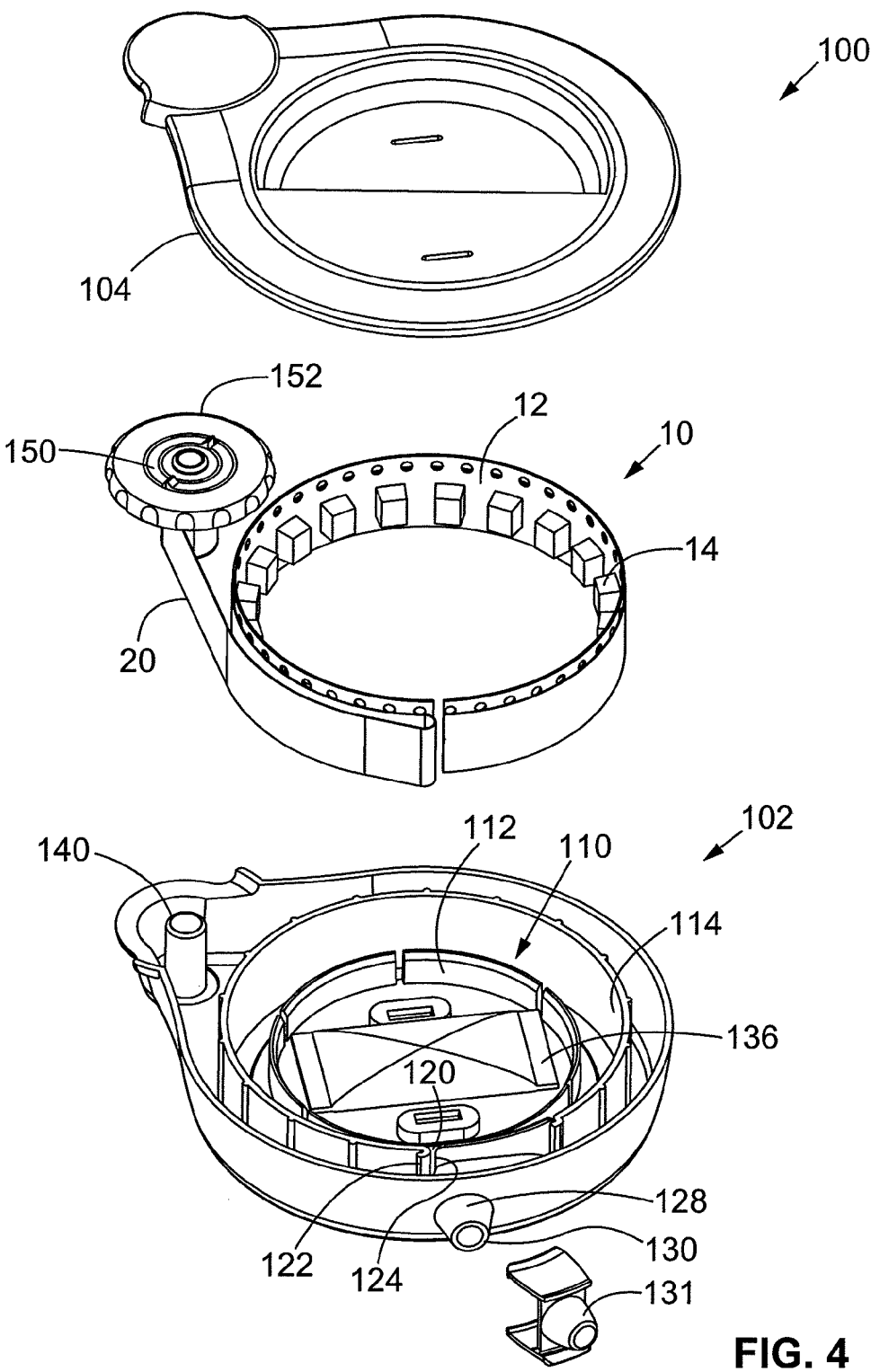
FIG. 4 is an exploded perspective view of a bead dispensing apparatus according to another embodiment of the present invention.

FIG. 4 is an exploded perspective view of a bead dispensing apparatus according to another embodiment of the present invention. The dispensing apparatus 100 includes a base 102 and a cover 104 which are connected to form a housing with an interior. The base 102 includes in the interior thereof a channel 110 in which to place the bead storage device 10 with the bead carrier 12 facing a support wall 112 of the channel 110 and the cover tape 20 facing a stripping wall 114 of the channel 110. The stripping wall 114 includes a stripping gap 120 disposed between a stripping edge 122 and an opposite edge 124, and a dispense opening 128 provided adjacent the opposite edge 124 on a side of the stripping wall 114 opposite from the stripping edge 122. In the embodiment shown, the stripping edge 122 includes a bend which bends outward from the channel 110 and backward away from the opposite edge 124 to guide the cover tape 20. The channel 110 is generally circular in shape. A spout 130 is desirably coupled to the dispense opening 128 and to be oriented generally downward to dispense the reagent beads 16 by gravity. The apparatus optionally includes a spout cap 131 for covering the spout 130 when the bead dispenser is not in use. FIG. 4 shows a desiccant 136 which may be placed inside the housing.

Figure 5:
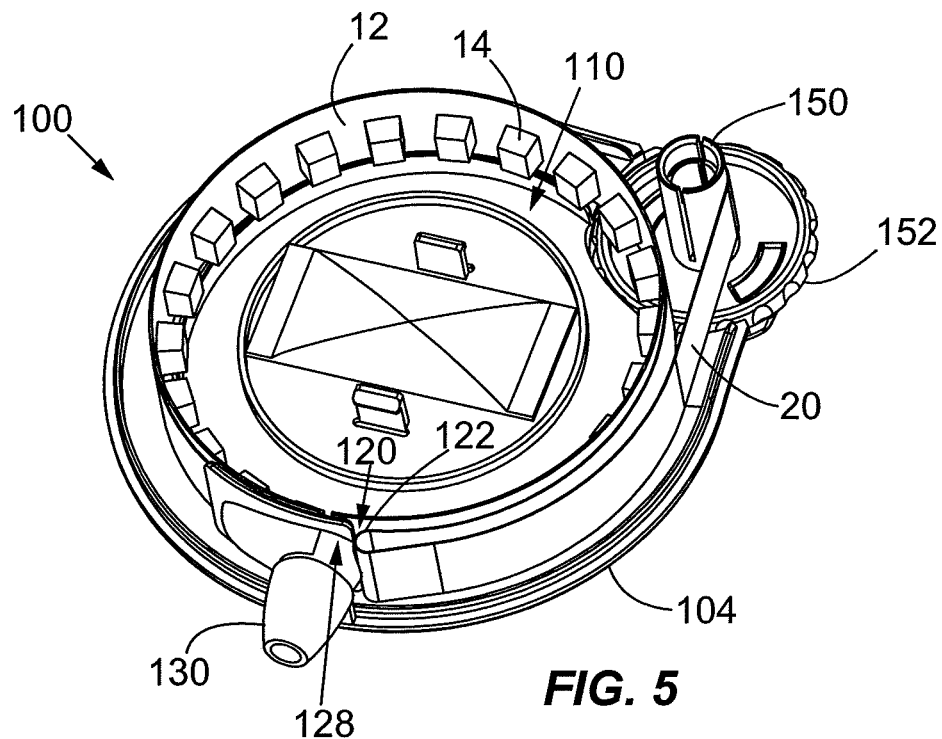
FIG. 5 is a perspective view showing the interior of the bead dispensing apparatus of FIG. 4.
Figure 6:
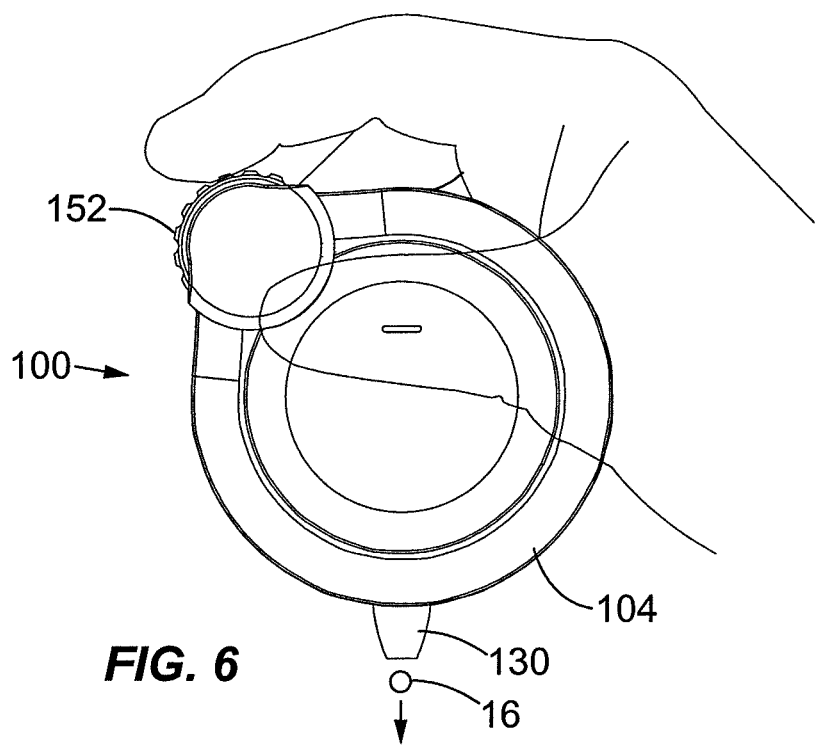
FIG. 6 is an elevational view of the bead dispensing apparatus of FIG. 4.

A shaft 140 is provided in the base 102 to support a clutch 150 which is configured to grip and pull a leading end of the cover tape 20 inserted through the stripping gap 120 to pull the cover tape 20 against the stripping edge 122. A wheel 152 is coupled to the clutch 150 for turning the clutch 150 to pull the cover tape 20. The wheel 152 may include a corrugated surface for easier turning by the finger of a user. The clutch 150 preferably includes a ratchet mechanism to permit one-directional pulling of the cover tape 20. The ratchet mechanism may include a gear and a pawl. As seen in FIGS. 5 and 6, the wheel 152 is preferably exposed from the interior of the housing and sized to be rotatable by a user's finger or thumb.

As seen in FIG. 5, the clutch 150 is configured to pull the leading end of the cover tape 20 inserted through the stripping gap 120 against the stripping edge 122 to peel the cover tape 20 from the bead carrier 12 to move the wells 14 of the bead carrier 12 inside the channel 110 toward the dispense opening 128 with the spout 130 and expose the wells 14 individually one at a time to dispense the reagent beads 16 from the wells 14 through the dispense opening 128 and the spout 130. To avoid accidentally dispensing beads, the wheel 152 is preferably configured to turn by a preset angle to move from one well to a next well toward the dispense opening 128 and expose the next well to dispense through the dispense opening 128 and spout 130. For example, the preset angle is preferably at least about 60°, and more preferably about 90-120°. A counter may optionally be coupled to the clutch 150 which is connected to a portion of the cover tape 20 that has been peeled from the bead carrier 12 to count the number of wells 14 being exposed to dispense the reagent beads 16 based on a travel amount of the cover tape 20 (as pulled by turning the clutch). In some embodiments, the housing of the apparatus 100 is transparent and has numbers 1 to X printed around its circumference, where X is the number of wells 14, to permit a user to see how many filled wells 14 remain by simple visual inspection.

FIG. 6 shows one example of dispensing beads by turning the wheel 152 by a user's finger to pull the cover tape. The spout 130 is oriented generally downward the dispense the beads 16 by gravity. In other embodiments, pulling of the cover tape can be performed by a machine either automatically or under the control of a user.

It is to be understood that the above description is intended to be illustrative and not restrictive. Many embodiments will be apparent to those of skill in the art upon reviewing the above description. The scope of the invention should, therefore, be determined not with reference to the above description, but instead should be determined with reference to the appended claims alone with their full scope of equivalents.

What is claimed is:

1. An apparatus for dispensing reagent beads, the apparatus comprising:
    a bead storage device comprising a bead carrier having two ends along its longitudinal axis and comprising a plurality of wells between the two ends;
    a plurality of reagent beads disposed in the plurality of wells; and
    a cover tape releasably attached to the bead carrier to cover the plurality of wells and retain the plurality of reagent beads in the plurality of wells, wherein two ends of the bead carrier are placed in a close proximity and the bead carrier is configured in a circular shape with the cover tape on the outside of the circular shape;
    a clutch located outside of the perimeter defined by the circular shape and connected to a leading end of the cover tape; and
    a housing enclosing the bead storage device with the cover tape facing a stripping wall of the housing;
    wherein the stripping wall is a continuous wall having a first end (a stripping edge) and a second end (an opposite edge), which are located in a close proximity to each other defining a stripping gap between the stripping edge and the opposite edge, and a dispense opening provided adjacent the opposite edge on a side of the stripping wall opposite from the stripping edge, the leading end of the cover tape is inserted through the stripping gap, wherein the clutch is configured to pull the leading end of the cover tape against the stripping edge to peel the cover tape from the bead carrier to move the plurality of wells of the bead carrier toward the dispense opening and expose the plurality of wells individually to dispense the plurality of reagent beads from the plurality of wells through the dispense opening.

2. The apparatus of claim 1, wherein the dispense opening is oriented generally downward and coupled to a spout to dispense the reagent beads by gravity.

3. The apparatus of claim 1, wherein the stripping edge includes a bend extending outward and backward away from the opposite edge to guide the cover tape.

4. The apparatus of claim 1, wherein the housing further comprises a support wall and a channel disposed between the support wall and the stripping wall.

5. The apparatus of claim 1, wherein the cover tape is insertable through the stripping gap to be pulled against the stripping edge to peel the cover tape from the bead carrier to move the plurality of wells of the bead carrier toward the dispense opening and expose the plurality of wells individually one at a time to dispense the reagent beads through the dispense opening.

6. The apparatus of claim 1, wherein the clutch includes a ratchet mechanism to permit one-directional pulling of the cover tape.

7. The apparatus of claim 1, further comprising a wheel coupled to the clutch for turning the clutch to pull the cover tape.

8. The apparatus of claim 1, further comprising a counter coupled to a portion of the cover tape which has been peeled from the bead carrier to count the number of wells being exposed to dispense the reagent beads based on a travel amount of the cover tape with respect to the stripping edge.

9. The apparatus of claim 1, wherein the clutch is configured to pull the leading end of the cover tape inserted through the stripping gap against the stripping edge to peel the cover tape from the bead carrier to move the plurality of wells of the bead carrier toward the dispense opening and expose the plurality of wells individually one at a time to dispense the reagent beads through the dispense opening.

10. The apparatus of claim 9, wherein the wheel is configured to turn by at least about 60° to move from one well to a next well toward the dispense opening and expose the next well to dispense the reagent bead through the dispense opening.

11. The apparatus of claim 1, further comprising a counter coupled to the clutch to count the number of wells being exposed to dispense the reagent beads based on a travel amount of the cover tape.

12. The apparatus of claim 1, wherein the clutch is directly connected to the leading end of the cover tape.

13. A method of dispensing reagent beads contained in a bead storage device, the device comprising:
   a bead carrier having two ends along its longitudinal axis and comprising a plurality of wells between the two ends;
   a plurality of reagent beads disposed in the plurality of wells; and
   a cover tape releasably attached to the bead carrier to cover the plurality of wells and retain the plurality of reagent beads in the plurality of wells, wherein two ends of the bead carrier are placed in a close proximity and the bead carrier is configured in a circular shape with the cover tape on the outside of the circular shape, the method comprising:
   placing the bead storage device in a housing comprising a stripping wall, with the cover tape facing the stripping wall, wherein the stripping wall is a continuous wall having a first end (a stripping edge) and a second end (an opposite edge), which are located in a close proximity to each other to define a stripping gap between the stripping edge and the opposite edge, and a dispense opening provided adjacent the opposite edge on a side of the stripping wall opposite from the stripping edge;
   inserting a leading end of the cover tape through the stripping gap and connecting the leading end to a clutch located outside of the perimeter defined by the circular shape; and
   pulling the leading end of the cover tape by the clutch against the stripping edge to peel the cover tape from the bead carrier to move the plurality of wells of the bead carrier toward the dispense opening and expose the plurality of wells individually to dispense the plurality of reagent beads from the plurality of wells through the dispense opening.

14. The method of claim 13, wherein the cover tape is pulled against the stripping edge in a direction generally opposite from a direction of travel of the bead carrier toward the dispense opening.

15. The method of claim 13, further comprising orienting the dispense opening generally downward with respect to the wells to dispense the reagent beads by gravity.

16. The method of claim 13, wherein the cover tape is pulled against the stripping edge to peel the cover tape from the bead carrier to move the plurality of wells of the bead carrier toward the dispense opening and expose the plurality of wells individually one at a time to dispense the reagent beads from the plurality of wells through the dispense opening.

17. The method of claim 16, further comprising counting the number of wells being exposed to dispense the reagent beads based on a travel amount of the cover tape with respect to the stripping edge.

18. The method of claim 13, wherein the clutch includes a ratchet mechanism to permit one-directional pulling of the cover tape.

19. The method of claim 13, wherein pulling the cover tape comprises turning a wheel coupled to the clutch.

20. The method of claim 13, wherein the clutch is directly connected to the leading end of the cover tape.

\* \* \* \* \*